US007189544B2

(12) United States Patent
Schmitt et al.

(10) Patent No.: US 7,189,544 B2
(45) Date of Patent: Mar. 13, 2007

(54) ENZYMATIC MODIFICATION OF LECITHIN

(75) Inventors: Heidi Schmitt, Aumuehle (DE); Marc Heirman, Kortrijk (BE)

(73) Assignee: Cargill, Incorporated, Wayzata, MN (US)

(*) Notice: Subject to any disclaimer, the term of this patent is extended or adjusted under 35 U.S.C. 154(b) by 0 days.

(21) Appl. No.: 10/822,222

(22) Filed: Apr. 9, 2004

(65) Prior Publication Data

US 2005/0227945 A1   Oct. 13, 2005

(51) Int. Cl.
*C12P 7/64* (2006.01)
(52) U.S. Cl. ............... 435/134; 435/132; 435/155; 435/41; 554/80; 426/534; 426/442; 426/478
(58) Field of Classification Search ............. 554/80; 987/233; 516/24, 28, 29, 56, 73; 435/132, 435/134, 197, 198
See application file for complete search history.

(56) References Cited

U.S. PATENT DOCUMENTS

| 4,584,141 | A | * | 4/1986 | Paulitz et al. | ............... 554/190 |
| 4,976,984 | A | * | 12/1990 | Yasukawa et al. | .......... 426/602 |
| 5,378,623 | A | * | 1/1995 | Hattori et al. | .............. 435/198 |
| 6,068,997 | A | * | 5/2000 | Sas et al. | ..................... 435/128 |
| 6,773,902 | B1 | * | 8/2004 | Chung et al. | ............... 435/128 |
| 2002/0122867 | A1 | * | 9/2002 | 't Hooft et al. | ............. 426/602 |
| 2003/0072856 | A1 | | 4/2003 | Jirjis | |
| 2003/0175383 | A1 | * | 9/2003 | Bojsen et al. | ................. 426/20 |

FOREIGN PATENT DOCUMENTS

| AU | 713557 | 11/1986 |
| WO | WO-00/52190 | 9/2000 |
| WO | WO 2005/024036 A2 | 3/2005 |

OTHER PUBLICATIONS

VanMiddlesworth et al, J. Org. Chem., 1992, vol. 57, pp. 4753-4754.*
Wikipedia, "Lecithin" http://en.wikipedia.org/wiki/Lecithin accessed on Oct. 4, 2005, 2 pages.*
Garrett et al, "Biochemistry" 1999 Saunders College Publishing, Second Edition, pp. 242-247.*
Hanahan et al, Journal of Biological Chemistry, 1960, vol. 235, No. 7, pp. 1917-1923.*
Bornscheuer, U.T. "Lipase-catalyzed syntheses of monacylglycerols" Enzyme and Mcirobial Technology, 1995, vol. 17, pp. 578-586.*
Bornscheuer, U.T., et al., "Optimizing lipases and related enzymes for efficient application," Trends in Biotechnology, vol. 20, No. 10, Oct. 2002, pp. 433-437.
Kilcawley, K.N., et al., "Determination of key enzyme activities in commercial peptidase and lipase preparations from microbial or animal sources," Enzyme and Microbial Technology, vol. 31, 2002, pp. 310-320.

Mustranta, A, et al., "Comparison of Lipases and Phospholipases in the Hydrolysis of Phospholipids," Process Biochemistry, vol. 30, No. 5, 1995, Great Britain, pp. 393-401.
Haas, M.J., et al., "The Hydrolysis of Phosphatidylcholine by an Immobilized Lipase: Optimization of Hydrolysis in Organic Solvents," Journal of the American Oil Chemists' Society, vol. 70, No. 2, Feb. 1993, pp. 111-117.
Haas, M.J., et al., "Enzymatic Phosphatidylcholine Hydrolysis in Organic Solvents: An Examination of Selected Commercially Available Lipases," Journal of the American Oil Chemists' Society, vol. 71, No. 5, May 1994, pp. 483-490.
Haas, M.J., et al., "The Enzymatic Hydrolysis of Triglyceride-Phospholipid Mixtures in an Organic Solvent," Journal of the American Oil Chemists' Society, vol. 72, No. 5, 1995, pp. 519-525.
Hara, F., et al., "Comparative Study of Commercially Available Lipases in Hydrolysis Reaction of Phosphatidylcholine," Journal of American Oil Chemists' Society, vol. 74, No. 9, 1997, pp. 1129-1132.
Gunstone, F.D., "Enzymes as biocatalysts in the modification of natural lipids," Journal of the Science of Food and Agriculture, vol. 79, No. 12, 1999, pp. 1535-1549.
Mustranta, A., et al., "Modification of Phospholipids With Lipases and Phospholipases," Biocatalysis, vol. 9, 1994, pp. 181-194.
Pearce, S.W. et al., "Lipases for food ingredients", 2002 Annual Meeting and Food Expo, Anaheim, California, XP-002337138, Session 94-5, 2002.
Pearce, S. et al., "Lipases for food ingredients", XP-002337138 Internet Abstract 94-5, 2002 Annual Meeting and Food Expo, Anaheim, California.
Chrisope, G. and Marchall, R., "Combined Action of Lipase and Microbial Phospholipase C on a Model Fat Globule Emulsion and Raw Milk", Journal of Dairy Science, 59(12):2024-2030, (1976).
Falcone, R. et al., "Effect of the Addition of a Nonaqueous Polar Solvent (Glycerol) on Enzymatic Catalysis in Reverse Micelles. Hydrolysis of 2-Naphthyl Acetate by—Chymotrypsin", Langmuir 20(14):5732-5737, (2004).
Gekko, K. and Timasheff, S., "Mechanism of Protein Stabilization by Glycerol: Preferential Hydration in Glycerol-Water Mixtures", Biochemistry 20(16):4667-4676, (1981).
Scow, R. and Egelrud, T., "Hydrolysis of Chylomichon Phosphatidylcholine In Vitro by Lipoprotein Lipase, Phospholipase $A_2$ and Phospholipase C", Biochimica et Biophysica Acta 431:538-549, (1976).

* cited by examiner

Primary Examiner—Leon B. Lankford, Jr.
Assistant Examiner—Allison M. Ford
(74) Attorney, Agent, or Firm—Perkins Coie LLP; Brian S. Boyer; Lee Ann Gorthey

(57) ABSTRACT

The disclosure pertains to enzymatic modification of lecithin and to hydrolyzed lecithin products obtained by such modification. One particular implementation provides methods for producing a hydrolyzed lecithin product containing hydrolyzed phospholipids, monoglycerides, and diglycerides. For example, such a method may include the steps of: (a) contacting a lecithin material, which includes a phospholipid component and a triglyceride component, in an aqueous or organic solvent medium, with a first enzyme effective to hydrolyze the phospholipid; and (b) subsequently contacting the product of step (a) with a second enzyme, effective to hydrolyze the triglyceride; under reaction conditions effective to inhibit esterification of the hydrolyzed phospholipid with released fatty acids.

41 Claims, No Drawings

ENZYMATIC MODIFICATION OF LECITHIN

FIELD OF THE INVENTION

The invention pertains to enzymatic modification of lecithin and to hydrolyzed lecithin products obtained by such modification.

REFERENCES

A. Bastida et al., A single step purification, immobilization, and hyperactivation of lipases via interfacial adsorption on strongly hydrophobic supports. *Biotechnology and Bioengineering* 58(5):486–493 (1998)

V. M. Balcao et al., Bioreactors with immobilized lipases: State of the art. *Enzyme and Microbial Technology* 18:391–416 (1995).

G. F. Bickerstaff, ed., Immobilization of Enzymes and Cells. Humana, Totawa, N.J., 1997.

U. T. Bornscheuer et al., Optimizing lipases and related enzymes for efficient application. *Trends in Biotechnology* 20(10):433–437 (2002).

O. Chmiel et al., Process for the interesterification of phospholipids. U.S. Pat. No. 5,989,599 (1999).

W. Cho et al., Efficient immobilization of phospholipase A2. *Methods in Molecular Biology* 109:303–307 (1999).

R. Fernandez-Lafuente et al., Immobilization of lipases by selective adsorption on hydrophobic supports. *Chemistry and Physics of Lipids* 93(1-2):185–97 (June 1998).

M. J. Haas et al., The hydrolysis of phosphatidylcholine by an immobilized lipase: optimization of hydrolysis in organic solvents. *Journal of the American Oil Chemists' Society* 70(2):111–17 (1993).

M. Haas et al., Enzymic phosphatidylcholine hydrolysis in organic solvents: an examination of selected commercially available lipases. *Journal of the American Oil Chemists' Society* 71 (5):483–90 (1994).

M. J. Haas et al., The enzymic hydrolysis of triglyceride-phospholipid mixtures in an organic solvent. *Journal of the American Oil Chemists' Society* 72(5):519–25 (1995).

F. Hara et al., Comparative study of commercially available lipases in hydrolysis reaction of phosphatidylcholine. *Journal of the American Oil Chemists' Society* 74(9):1129–1132 (1997).

F. D. Gunstone, Enzymes as biocatalysts in the modification of natural lipids. *Journal of the Science of Food and Agriculture* 79:1535–1549 (1999).

A. E. Ivanov et al., Methods for the immobilization of lipases and their use for ester synthesis. *Journal of Molecular Catalysis B: Enzymatic* 3:303–309 (1997).

B. Jirjis et al., Method for removing phospholipids from vegetable oil miscella, method for conditioning a polymeric microfiltration membrane, and membrane. U.S. Pat. No. 6,207,209 (2001).

B. Jirjis et al., Method and apparatus for processing vegetable oil miscella, method for conditioning a polymeric microfiltration membrane, membrane, and lecithin product. U.S. application Pubn. No. 2003/0072856 (2003).

S. T. Kang et al., Characteristics of immobilized lipase-catalyzed hydrolysis of olive oil of high concentration in reverse phase system. *Biotechnology and Bioengineering* 33(11):1469–76 (1989).

F. X. Malcata et al., Kinetics and mechanisms of reactions catalysed by immobilized lipases. *Enzyme and Microbial Technology* 14(6):426–46 (June 1992).

F. X. Malcata et al., Immobilized lipase reactors for modification of fats and oils—a review. *Journal of the American Oil Chemists Society* 67(12):890–910 (1990).

K. Mosbach, ed., *Methods in Enzymology*, Vol. 137: Immobilized Enzymes and Cells. Academic Press, San Diego, Calif., 1988.

A. Mustranta et al., Comparison of lipases and phospholipases in the hydrolysis of phospholipids. *Process Biochemistry* 30(5):393–401 (1995).

I. C. Omar et al., Hydrolysis of triglycerides by immobilized thermostable lipase from *Humicola lanuginosa*. *Agricultural and Biological Chemistry* 52(1):99–105 (1988).

M. V. Ramachandra et al., Hydrolysis of oils by using immobilized lipase enzyme: A review. *Biotechnology and Bioprocess Engineering* 7(2):57–66 (2002).

B. Sas et al., Improved method for the conversion of lecithin into lysolecithin. PCT Pubn. No. WO 00/52190 (2000).

J. F. Shaw et al., Lipolytic activities of a lipase immobilized on six selected supporting materials. *Biotechnology and Bioengineering* 35(2):132–7 (1990).

BACKGROUND OF THE INVENTION

Lecithins and modified lecithins are widely used in the food and pharmaceutical industries as digestible solubilizers and emulsifiers. Lecithins are obtained from various animal or vegetable sources, such as soybeans or egg yolk, and comprise a mixture of phospholipids and triglycerides, as well as lesser amounts of compounds such as glycolipids, carbohydrates, fatty acids, and/or sterols.

Partial hydrolysis of phospholipids in lecithins has been found to improve emulsifying properties. This modification is most commonly effected by treatment of lecithin with phospholipase A1 and/or A2, which selectively hydrolyze the first or second glyceryl fatty acid, respectively, of phospholipids.

Addition of mono- and diglycerides to lecithins or partially hydrolyzed lecithins has also been found to improve properties in end products, such as antisplattering properties in margarines or baking characteristics in flour. Currently, such products are prepared by adding such mono- and diglycerides to lecithins or partially hydrolyzed lecithins. It would be useful to directly prepare such products, in a controlled manner, by enzymatic hydrolysis of lecithin.

DETAILED DESCRIPTION OF THE INVENTION

I. Overview

The invention provides, in one aspect, methods for producing a hydrolyzed lecithin product, containing hydrolyzed phospholipids, monoglycerides, and diglycerides. One such method is a two-enzyme method comprising the steps of:

(a) contacting a lecithin material, comprising a phospholipid component and a triglyceride component, in an aqueous or organic solvent medium, with a first enzyme effective to hydrolyze the phospholipid; and (b) subsequently contacting the product of step (a) with a second enzyme, effective to hydrolyze the triglyceride;

under reaction conditions effective to inhibit esterification of the hydrolyzed phospholipid with released fatty acids.

The solvent medium may be either an aqueous medium, i.e. consisting primarily of water, or an organic solvent medium, comprising an aprotic organic solvent. The organic solvent is preferably a hydrocarbon solvent. In this case, the lecithin starting material is preferably a retentate from a vegetable oil membrane degumming process, as described further below.

In a related two-enzyme process, the method comprises:
contacting a lecithin material, comprising a phospholipid component and a triglyceride component, in an aprotic organic solvent, with a first enzyme effective to hydrolyze the phospholipid, and a second enzyme effective to hydrolyze the triglyceride, under conditions effective to inhibit esterification of the hydrolyzed phospholipid with released fatty acids. In this process, the lecithin material may be contacted with the first and second enzymes simultaneously, or they may be added in sequence, such that the lecithin material is contacted with the first enzyme and subsequently contacted with the second enzyme. In the latter case, the isolated reaction product of the first enzyme reaction may be contacted with the second enzyme.

In the above processes, the first enzyme is, preferably, a phospholipase, or it may be a phospholipid reactive lipase. Preferred phospholipases include phospholipase A1 and/or A2, particularly phospholipase A2. In other embodiments, the phospholipase is phospholipase D. In the latter case, a preferred process includes, prior to reaction with the second enzyme (lipase), contacting the reaction product of the phospholipase D reaction with phospholipase A1 and/or A2, preferably phospholipase A2.

The second enzyme, which in all cases is different from the first enzyme, is a lipase. This lipase is preferably effective to selectively hydrolyze the triglyceride, as defined herein, under the given reaction conditions.

The invention also provides, in a further aspect, a single-enzyme method for producing a hydrolyzed lecithin product which contains phospholipids, monoglycerides, and diglycerides, and may also include triglycerides. Such a method comprises contacting a lecithin material as defined herein, comprising a phospholipid component and a triglyceride component, with a lipase which is effective to selectively hydrolyze the triglyceride. This process is directed to selective hydrolysis of the triglyceride component of the lecithin starting material, and preferably minimizes hydrolysis of the phospholipid component. Accordingly, no phospholipase is present.

As above, the solvent medium may be either an aqueous medium, i.e. consisting primarily of water, or an organic solvent medium, comprising an aprotic organic solvent. The organic solvent is preferably a hydrocarbon solvent. In this case, the lecithin starting material is preferably a retentate from a vegetable oil membrane degumming process, as described further below.

In selected embodiments of the above processes, particularly in reactions employing an organic solvent medium, the process is carried out in the presence of a membrane effective to separate phospholipids, hydrolyzed phospholipids, monoglycerides, diglycerides and triglycerides from released fatty acids:

The hydrolyzed lecithin product of the above processes preferably comprises at least 56%, more preferably at least 60%, acetone insoluble materials, and has an acid value of less than 45 mg KOH/gram.

In another aspect, the invention provides a hydrolyzed lecithin product, containing phospholipids and/or hydrolyzed phospholipids, monoglycerides, and diglycerides. The product may also contain triglycerides. The product comprises at least 56%, preferably at least 60%, acetone insoluble materials, and has an acid value of less than 45 mg KOH/gram. Preferably, it contains at least 15%, more preferably at least 30% by weight mono/diglycerides. The hydrolyzed lecithin product can be produced by any of the above described processes of the invention, followed by removal or deactivation of enzymes and removal of solvent. Preferably, the product is produced by a method employing first and second enzymes as described above.

Preferably, the hydrolyzed lecithin product of the invention consists essentially of components of the lecithin starting material of the above processes and hydrolyzed substances which are obtained from the lecithin starting material by reaction of the above-described enzymes.

II. Processes for Enzymatic Modification of Lecithin

The invention provides methods for producing a hydrolyzed lecithin product, where the components of the product include phospholipids and/or hydrolyzed phospholipids, monoglycerides, and diglycerides (the last two components referred to jointly as mono/diglycerides). Typically, the product includes unhydrolyzed phospholipids and triglycerides. The hydrolyzed phospholipids are typically lysophospholipids, and may also include phosphatidic acid and/or lysophosphatidic acid.

In accordance with the invention, the hydrolyzed lecithin product is produced directly by enzymatic treatment of lecithin, without the need for separate addition of any of the above named components. In preferred embodiments, the process produces a hydrolyzed lecithin product comprising at least 56%, and more preferably at least 60%, acetone insoluble materials (i.e. phospholipids and/or hydrolyzed phospholipids) and having an acid value of less than 45 mg KOH/gram.

The process employs a lecithin starting material having a phospholipid component (preferably at least 50%, and more preferably at least 60%, by weight) and a triglyceride component. Commercially produced lecithins in general fit this description. As used herein, a "lecithin material" or "lecithin starting material" refers to a lecithin derived, from a naturally occurring material, such as egg yolk or vegetable oil, e.g. soybean oil, using conventional processing methods, such as described below. The lecithin starting material may include a solvent.

Commercial lecithins are most commonly produced from processing of crude soybean oil. In a typical process, soybeans are dehulled and extracted with hexane to produce an extractant (miscella) which includes hexane and crude soybean oil. The crude soybean oil contains, as a major component, glyceride oil, in addition to phospholipids, sugars, sterols, sterol glucosides, fatty acids, and other components in minor amounts. The phospholipids are solubilized in the hexane solvent by the formation of large micellar aggregates.

Phospholipids are separated from the majority of the glyceride oil in the miscella in a process known as "degumming". In conventional water degumming, this is generally done by removing the hexane solvent, hydrating the phospholipids with hot water or steam, which renders them insoluble in hexane, and centrifuging. Removal of some or all of the water gives a crude lecithin material, typically containing about 60–65% phospholipids (acetone insolubles), with the remainder primarily glycerides, and minor amounts of other components, such as sugars, sterol glucosides, and/or fatty acids.

More recently, methods have been developed for membrane degumming of soybean oil; see, for example, Jirjis et al., U.S. Pat. No. 6,207,209. In a preferred embodiment of the invention, the lecithin starting material is provided by such a process. In membrane degumming, a vegetable oil miscella in a hydrocarbon solvent is fed to a membrane, producing a permeate stream which is depleted in phospholipids and a retentate stream which is enriched in phospholipids, relative to the phospholipid content of the miscella. The retentate is essentially a lecithin solution in the processing solvent, which is typically hexane. This retentate can be used as a starting material in the present processes. The phospholipid content of such a retentate can be up to about 85% (Jirjis et al., 2003), and it generally contains fewer impurities than lecithins obtained via water degumming.

In the two-enzyme process of the invention, a phospholipase (or a phospholipid reactive lipase) is used to hydrolyze phospholipids in the lecithin starting material to lysophospholipids and/or phosphatidic acids, and a separate lipase is used to hydrolyze triglycerides to mono/diglycerides. By employing the two different enzymes, the amounts of the different hydrolyzed components, particularly the mono/diglycerides, in the final product can be controlled. The process is carried out under conditions, such as described below, effective to inhibit transesterification of hydrolyzed phospholipids with released fatty acids.

As described further below, the reaction, when carried out in aqueous solvent, advantageously employs a phospholipase enzyme in a first stage, and the lipase enzyme in a later stage. Reaction in organic solvent can employ both enzymes sequentially or simultaneously. Such reaction can be performed directly on a retentate from a membrane degumming process, as described further below.

Reaction of lipases and phospholipases with their substrates is known to occur at a lipid-water interface (e.g. L. Brady et al., *Nature* 343:767, 1990); accordingly, the reaction can be carried out on lipid substrates in water (aqueous medium), where the substrates are generally present in the form of aggregates such as micelles or vesicles. An "aqueous medium", as used herein, refers to a solvent medium containing water and at most 10%, more preferably at most 5%, of another water-miscible solvent. Preferably, the aqueous medium does not contain another water-miscible solvent.

The reaction can also be carried out in an organic solvent medium. As used herein, the term "organic solvent medium" refers to an organic solvent, preferably an aprotic solvent (i.e. not an alcohol or amine), but it is understood that the reaction medium includes sufficient water content for hydrolysis to occur. Preferably, the water content is at a level effective to promote hydrolysis and minimize transesterification. This water may be added to the reaction medium, e.g. by using a water saturated solvent, or it may be provided by entrapped or residual water in the lecithin starting material.

A. Reaction in Aqueous Medium

In one embodiment, the process is carried out in an aqueous medium, as defined above. The starting material for such a reaction may be a crude lecithin material obtained from water degumming of soybean oil. However, any lecithin starting material, including lecithin obtained from a membrane degumming process, as described below, can be used in aqueous medium.

When the process is carried out in an aqueous medium, reaction of the lipase to selectively hydrolyze triglycerides can lead to a large increase in the viscosity of the medium. Accordingly, when the two-enzyme process is carried out in an aqueous medium, it is preferable that the lecithin starting material is first contacted with the phospholipase (or phospholipid reactive lipase) enzyme, and, after sufficient time for reaction and, optionally, recovery of an intermediate product, subsequently contacted with the (triglyceride selective) lipase enzyme. Examples of such processes are provided below.

The two-enzyme process is carried out under conditions effective to inhibit transesterification of the hydrolyzed phospholipid with released fatty acids. For example, a salt or weak base may be added to the reaction mixture to sequester the released fatty acids. Such a salt may be, for example, excess calcium chloride. Calcium chloride is routinely included as an ionic activator in reactions employing phospholipases.

Alternatively or in addition, the reaction may be carried out in the presence of a membrane having a composition and pore size effective to remove fatty acids from the reaction mixture.

As discussed further below, the enzymes may be immobilized, which facilitates their removal from the reaction mixture. Alternatively, enzymes that are not immobilized are inactivated at the completion of reaction, e.g by heat treatment.

B. Reaction in Organic Solvent

The process may also be carried out in an organic solvent medium, preferably an aprotic solvent, containing sufficient water for hydrolysis to take place, and preferably sufficient water to promote hydrolysis and inhibit transesterification. The starting material lecithin is provided in the organic solvent. In one embodiment, the process is carried out on a retentate obtained in membrane degumming of soybean oil. The retentate, as described, for example, in U.S. Pat. No. 6,207,209 and related U.S. Appn. No. 2003/0072856, both to Jirjis et al., contains the majority of the phospholipids present in the preprocessed oil, since these compounds form large aggregates in the hydrocarbon solvent which do not penetrate the membrane pores. The retentate also contains a significant fraction of triglycerides.

The organic solvent can be any solvent which is inert to the reaction conditions, including, for example, low molecular weight esters or ketones, halogenated hydrocarbons, or, preferably, hydrocarbons. Preferred hydrocarbon solvents include alkanes, cycloalkanes, and simple aromatic hydrocarbons, e.g., benzene and its homologs containing alkyl substituents having up to four carbon atoms. Exemplary hydrocarbons include benzene, toluene, xylenes, $C_3$–$C_6$ cycloalkanes, $C_5$–$C_8$ alkanes, mixtures thereof, e.g. petroleum ether, and $C_5$–$C_8$ alkenes.

When the two-enzyme process is carried out in an organic solvent, the first and second enzymes may be added sequentially, as described above, with optional isolation of the intermediate lecithin product before addition of the second enzyme. Alternatively, when an organic solvent medium is used, the first and second enzymes may be added simultaneously. Examples of both types of reactions are provided below.

The two-enzyme process is carried out under conditions effective to inhibit transesterification of hydrolyzed phospholipid with released fatty acids. Preferably, the water content of the reaction is effective to promote hydrolysis over transesterification. In addition, a salt or weak base may be added to the reaction mixture to sequester the released fatty acids. Such a salt may be, for example, excess calcium chloride. Calcium chloride is routinely included as an ionic activator in reactions employing phospholipases.

The process can be carried out, particularly when done in an organic solvent, in the presence of a membrane effective to separate the lecithin product components, e.g. phospholipids, hydrolyzed phospholipids, triglycerides, monoglycerides, and diglycerides, from released fatty acids. A suitable membrane composition, pore size, and operating pressure can be selected, according to methods known in the art, to allow the free fatty acids to selectively pass through the membrane.

Again, as discussed further below, the enzymes may be immobilized, which facilitates their removal from the reaction mixture. Non-immobilized enzymes are deactivated following completion of the reaction, typically by heating.

II. Enzymes

A. Phospholipases

As described above, the methods of the invention may employ a phospholipase to hydrolyze phospholipids in the starting material. Phospholipases are categorized as A1, A2, C, and D on the basis of which bond in a phospholipid is hydrolyzed by the enzyme, as indicated below. The present process typically employs phospholipase A1 (EC 3.1.1.32) and/or A2, preferably phospholipase A2 (EC 3.1.1.4), which produces lysophospholipids by removal of an acyl side chain. In some embodiments, a phospholipase D (EC 3.1.4.4) may be used, alone or in combination with phospholipase A1 or A2, to provide phosphatidic acids and/or lysophosphatidic acids.

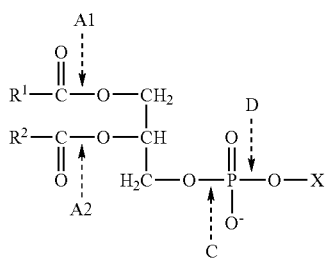

Hydrolysis of lecithins with phospholipases alone is well known in the art. See, for example, GB Patent No. 1215868 (1970), which describes a conventional process in which lecithin is reacted with phospholipase A2 in aqueous emulsion, in the presence of calcium ions, to provide lysolecithin. Purification includes extraction with acetone, which removes acetone soluble materials such as fatty acids and glycerides. Hirai et al. (U.S. Pat. No. 5,955,327) describes reaction of hydrated lecithin with phospholipase A1 or A2 in aqueous medium, followed by partitioning with acetone to isolate the lysolecithin product. Yesair (U.S. Pat. No. 5,716,814) describes a process in which a mixture of phosphatidyl choline and a monoglyceride are reacted with phospholipase A2, to yield a lysophospholipid-monoglyceride-fatty acid composition.

Phospholipase enzymes are readily available commercially, e.g. Lecitase™ (phospholipase A2) as provided by Novo Nordisk and phospholipase A1 as provided by Sankyo Pharma. In selected embodiments, as described further below, phospholipase D is used alone or in combination with phospholipase A1 or A2, preferably A2, to produce hydrolyzed lecithin products having a phosphatidic acid or lysophosphatidic acid component. It may also be used in combination with an alcohol selected from ethanolamine, serine, and inositol, to increase, respectively, the PE, PS, or PI content of the lecithin product. Examples of such processes are provided below.

B. Lipases

Many different lipases (also referred to as triacylglycerol hydrolases; EC 3.1.1.3), obtained from animal, plant, or microbial sources, are known and/or commercially available, often in immobilized form. These enzymes can vary widely in selectivity; that is, in the degree of lipase activity, phospholipase activity, and/or esterase activity exhibited by a particular enzyme preparation.

Information regarding activity of a commercial lipase preparation will often be provided by the manufacturer. In general, however, enzyme activity and selectivity can vary with reaction conditions, e.g. whether the reaction is done in organic or aqueous medium, whether the enzyme is immobilized, etc., and with the purity of the particular preparation. Other parameters that can affect reactivity and selectivity of an enzyme include pH, substrate concentration, and solvent polarity (see e.g. Haas et al., 1995, 1994; cited above).

The activity of a particular enzyme preparation with respect to different substrates, such as phospholipids and triglycerides, can be evaluated empirically for a given set of reaction conditions, if desired, using methods known in the art. For example, A. Mustrata et al. (cited above) determined the degree of hydrolysis of soy phosphatidyl choline (i.e., phospholipase activity) for each of various lipases and phospholipases, in aqueous emulsion, by titration of released fatty acids produced by 30 minutes of reaction. Similar reaction with olive oil was used to determine lipase activity. In this report, an *A. niger* lipase and a *P. cyclopium* lipase both showed significant phospholipase activity, though lipase activity was higher, particularly for the *A. niger* lipase. The report also found the phospholipase A2 preparations to be much more phospholipase selective than the phospholipase A1 preparations.

M. Haas et al. (1995, cited above) determined the degree of hydrolysis of phospholipids and triglycerides, separately and in mixtures, by each of three lipases and one phospholipase, each commercially available in immobilized form. Degree of hydrolysis was determined by titration of released fatty acids and by HPLC analysis of the product lipid mixtures. Solvent medium (i.e. water or water-saturated hexane) was found to have a large effect on reactivity and selectivity in this report. For example, lipases from *R. miehei* and *C. rugosa* were much more reactive towards triglycerides than towards phospholipids in both solvent media, and a third lipase, from *C. antarctica,* showed similar selectivity to *R. miehei* in water but was unreactive in hexane. The phospholipase (Amano phospholipase B) was unreactive in water and hydrolyzed only the phospholipids in hexane.

In another analysis, F. Hara et al. (cited above) determined the degree of hydrolysis of phosphatidyl choline by various lipases in a reverse micellar system over 24 hrs and over 48 hrs. The degree of hydrolysis, determined by chromatographic analysis, varied from 0 to 100% for the lipases tested. For example, under the reaction conditions described, lipases derived from *M. javanicus* (Lipase M10, Amano Pharmaceuticals), *M. miehei* (Lipozyme IM20, Novo Nordisk), and hog pancreas (Pancreatin F, Amano) gave 100% hydrolysis of phosphatidyl choline; lipases derived from *Rhizopus* sp. (Lipase F, Amano) and *R. delemar* (Newlase F, Amano) gave about 35–45% hydrolysis; and lipases derived from *A. niger* (Lipase A6, Amano) and *C. cylindrica* (Lipase AY30, Amano) gave little or no hydrolysis.

As shown in the above-cited articles and others in the field, lipases often exhibit significant phospholipase activity. Such enzymes, which may be referred to as "phospholipid reactive" lipases herein, may be used as the first enzyme in the two-enzyme processes described herein. A lipase which is "phospholipid reactive" may be defined as one which, under suitable reaction conditions such as those set forth in the exemplary reactions below, is effective to hydrolyze at least 25%, more preferably at least 50%, of phospholipids present in the reaction. Such reaction conditions may include reaction in an aqueous medium, employing 0.001 to 0.2% enzyme based on 60% AI (acetone insolubles), at about 40–60° C. for 4 to 24 hours, or reaction in an organic solvent, employing the same level of enzyme, at about 20–60° C. for 1 to 24 hours.

More typically, the first enzyme in the two-enzyme reaction is a phospholipase, and lipases are employed as the second enzyme in the two-enzyme processes described herein, or as the single enzyme in processes targeting selective hydrolysis of the triglyceride component of the lecithin starting material. For these purposes, preferred lipases can be defined as those which, under the given reaction conditions, are selective for lipase activity; that is, the degree of hydrolysis of acyl glycerols by the lipase is greater than the degree of hydrolysis of acyl phospholipids by the lipase. More preferably, the degree is about 5 times greater, most preferably about 25 or about 50 times greater. Degree of hydrolysis may be defined as moles of fatty acid generated in a given reaction time under the specified conditions, and compared for reaction of the enzyme with a phospholipid vs. reaction with a triglyceride.

As noted above, reaction conditions include, for example, solvent, state of enzyme (e.g. whether immobilized or not), temperature, pH, presence and concentration of ionic additives, and substrate concentration.

C. Immobilization of Enzymes

The lipase and/or the phospholipase may be immobilized, for which various materials and methods are known in the art. Enzyme immobilization, in general, prolongs the useful life of the enzymes, simplifies purification of the products, and often enhances the catalytic activity of the enzyme. Materials onto which enzymes have been immobilized include silica, porous glass, Celite®, diatomaceous earth, ion exchange resins, and various other polymeric substrates including polyamides, polypropylene, polyethylene glycol, polysaccharides such as cellulose and agarose, and alkyl modified agarose. Polymeric substrates may be provided, for example, in the form of membranes, hollow fibers, or beads. In one embodiment, a membrane used for separation of fatty acids in the reaction could also be used for immobilization of enzymes. Immobilization is frequently accomplished by simple adsorption but may include covalent attachment, e.g. to amino or aldehyde modified silica.

Extensive descriptions of enzyme immobilization, including particular description of lipase and phospholipase immobilization, are available in the literature. A sampling of references includes K. Mosbach, ed., 1988; F. X. Malcata et al., 1990, 1992; V. M. Balcao et al., 1995; A. E. Ivanov et al., 1997; G. F. Bickerstaff, ed., 1997; Bastida et al., 1998; R. Fernandez-Lafuente et al., 1998; W. Cho et al., 1999; U. T. Bornscheuer et al., 2002; M. V. Ramachandra et al., 2002; all cited above under "References". Enzymes are frequently provided commercially in immobilized form.

III. Hydrolyzed Lecithin Product

The invention also provides a hydrolyzed lecithin product containing phospholipids and/or hydrolyzed phospholipids, monoglycerides, and diglycerides, and typically containing phospholipids and triglycerides. Preferably, the hydrolyzed lecithin product contains at least 15% by weight, and more preferably at least 30% by weight, mono/diglycerides. In various embodiments, the hydrolyzed lecithin product contains at least 1%, at least 5%, at least 10%, at least 15%, at least 20%, at least 25%, at least 30%, at least 35%, at least 40%, or at least 45% mono/diglycerides. In one embodiment, the hydrolyzed lecithin product contains about 30% to about 45% mono/diglycerides. The hydrolyzed phospholipids may include lysophospholipids, phosphatidic acid, and/ or lysophosphatidic acid. Preferably, the hydrolyzed lecithin product contains a minimal amount, e.g. less than 5%, of transesterification products; that is, products of the reaction of said lysophospholipids with released fatty acids.

According to the E322 labeling standard, "lecithins" are defined as "mixtures of fractions of phospholipids which are obtained from animal or vegetable foodstuffs by physical processes"; they may also include "hydrolyzed substances which are obtained by the use of harmless and suitable enzymes". "Lecithins", according to this standard, must include at least 60% acetone insoluble substances and have an acid value of less than 35 mg KOH/gram, while "hydrolyzed lecithins" must include at least 56% acetone insoluble substances and have an acid value of less than 45 mg KOH/gram.

The hydrolyzed lecithin product of the invention is derived from a lecithin starting material, as described above, which contains mixtures of fractions of phospholipids which are obtained from animal or vegetable foodstuffs by physical processes. The lecithin starting material may be obtained, for example, from water degumming or membrane degumming of crude soybean oil. The lecithin starting material preferably meets the E322 labeling standard for lecithin, in that it contains at least 60% acetone insoluble substances and has an acid value of less than 35 mg KOH/gram. Standard methods for determining these parameters are outlined below.

The hydrolyzed lecithin product of the invention consists essentially of components of this lecithin starting material and hydrolyzed substances which are obtained from the lecithin starting material by the use of harmless and suitable enzymes, specifically, a lipase and, in most instances, a phospholipase, as described herein. By "consists essentially of" is meant that the hydrolyzed lecithin product may contain, for example, water, but it does not contain lipid components other than the components and hydrolyzed substances specified above. It does not contain residual enzyme activity. The hydrolyzed lecithin product of the invention meets the standards of E322 for hydrolyzed lecithins, in that it includes at least 56% acetone insoluble substances and has an acid value of less than 45 mg KOH/gram.

IV. Exemplary Reactions

The following reactions are exemplary only and are not intended to limit the invention.

As noted above, by employing two different enzymes, one, preferably a phospholipase, for hydrolysis of phospholipids, and a triglyceride selective lipase for hydrolysis of triglycerides, the amounts of the different hydrolyzed components, particularly mono/diglycerides, in the final product can be controlled. Reaction in aqueous solvent advantageously employs a phospholipase enzyme in a first stage, and a triglyceride-selective lipase enzyme in a later stage, due to increases in viscosity that can be expected during reaction with the lipase. Reaction in an organic solvent can employ both enzymes sequentially or simultaneously.

Alternatively, a hydrolyzed lecithin product containing phospholipids and mono-diglycerides is obtained by treatment of the starting material with a triglyceride-selective lipase.

A. Reaction in Aqueous Medium; Sequential Addition of Enzymes

A fluid lecithin having an acetone insoluble (AI) level of 55%–75% is combined with water, in an amount of 0.1 to 10%, preferably about 5–8% based on 60% AI, and phospholipase A2, in an amount of 0.001 to 0.2% based on 60% AI. While the amount of enzyme used is dependent on the activity of the particular enzyme, a typical amount of Lecitase™ employed would be about 0.017%. If necessary, the pH is adjusted to a level favorable to the enzyme by adding Tris HCl, and $CaCl_2$ is added to activate the enzyme. Excess $CaCl_2$ may be used to efficiently sequester released fatty acids. Reaction is carried out at about 40–60° C. for 4 to 24 hours. Drying provides a product containing lysolecithin, in an amount determined by reaction time and temperature and enzyme concentration.

To this product is added a lipase, in an amount of 0.001 to 0.2%, preferably 0.1 to 0.2%, based on 60% AI. If necessary, the pH is adjusted to a level favorable to the enzyme by adding Tris HCl, and $CaCl_2$ is added. Reaction is carried out at about 40–60° C. for 4 to 24 hours. Drying provides a lecithin product containing lysolecithin and also containing mono/diglycerides, in an amount determined by reaction time and temperature and enzyme concentration.

Preferably, the lipase concentration and other parameters are effective to produce a hydrolyzed lecithin product containing at least 15%, and more preferably at least 30%, mono/diglycerides.

B. Hydrolysis in Organic Solvent: Sequential Addition of Enzymes

A fluid lecithin obtained as the retentate from a membrane degumming process, as described, for example, in U.S. Pat. No. 6,207,209, having an acetone insoluble (AI) level of 55%–80%, is combined with phospholipase A2, which may be immobilized, in an amount of 0.001 to 0.2%, based on 60% AI. If necessary, the pH is adjusted to a level favorable to the enzyme by adding Tris HCl, and $CaCl_2$ is added to activate the enzyme. Excess $CaCl_2$ may be used to efficiently sequester released fatty acids. Reaction is carried out at about 20–60° C. for 1 to 24 hours. Immobilized enzyme is recovered, and drying provides a product containing lysolecithin, in an amount determined by reaction time and temperature and enzyme concentration.

To this product is added a lipase, which may be immobilized, in an amount of 0.001 to 0.2%, preferably 0.1 to 0.2%, based on 60% AI. If necessary, the pH is adjusted to a level favorable to the enzyme by adding Tris HCl, and $CaCl_2$ is added. Reaction is carried out at about 20–60° C. for 1 to 24 hours. Immobilized enzyme is recovered, and drying provides a lecithin product containing lysolecithin and also containing mono/diglycerides, in an amount determined by reaction time and temperature and enzyme concentration.

In a preferred embodiment, the reaction is carried out in the presence of a membrane having a composition and pore size effective to selectively remove fatty acids from the reaction mixture.

Preferably, the lipase concentration and other parameters are effective to produce a hydrolyzed lecithin product containing at least 15%, and more preferably at least 30%, mono/diglycerides.

C. Hydrolysis in Organic Solvent: Simultaneous Addition of Enzymes

A fluid lecithin obtained as the retentate from a membrane degumming process, as described, for example, in U.S. Pat. No. 6,207,209, having an acetone insoluble (AI) level of 55%–80%, is combined with phospholipase A2 and a triglyceride selective lipase, each of which may be immobilized, each in an amount of 0.001 to 0.2%, based on 60% AI. If necessary, the pH is adjusted to a level favorable to the enzymes by adding Tris HCl, and $CaCl_2$. Excess $CaCl_2$ may be used to efficiently sequester released fatty acids. The reaction is carried out at about 20–60° C. for 1 to 24 hours. In a preferred embodiment, the reaction is carried out in the presence of a membrane having a composition and pore size effective to selectively remove fatty acids from the reaction mixture.

Immobilized enzyme is recovered, and drying provides a lecithin product containing lysolecithin and mono/diglycerides, each in an amount determined by reaction time and temperature and respective enzyme concentration. Preferably, the lipase concentration and other parameters are effective to produce a hydrolyzed lecithin product containing at least 15%, and more preferably at least 30%, mono/diglycerides.

D. Reaction in Aqueous Medium: Sequential Addition of Phospholipase D and Lipase A fluid lecithin having an acetone insoluble (AI) level of 55%–75% is combined with water, in an amount of 0.1 to 10% based on 60% AI, and phospholipase D, in an amount of 0.0001 to 0.5% based on 60% AI. If necessary, the pH is adjusted to a level favorable to the enzyme by adding Tris HCl, and $CaCl_2$ is added to activate the enzyme. Excess $CaCl_2$ may be used to efficiently sequester released fatty acids. Reaction is carried out at about 40–60° C. for 4 to 24 hours. Drying provides a product containing phosphatidic acid, in an amount determined by reaction time and temperature and enzyme concentration.

To this product is added a lipase, in an amount of 0.001 to 0.2%, preferably 0.1 to 0.2%, based on 60% AI. If necessary, the pH is adjusted to a level favorable to the enzyme by adding Tris HCl, and $CaCl_2$ is added. Reaction is carried out at about 40–60° C. for 4 to 24 hours. Drying provides a lecithin product containing phosphatidic acid and also containing mono/diglycerides, in an amount determined by reaction time and temperature and enzyme concentration.

Preferably, the lipase concentration and other parameters are effective to produce a hydrolyzed lecithin product containing at least 15%, and more preferably at least 30%, mono/diglycerides.

E. Reaction in Aqueous Medium; Sequential Addition of Phospholipase D, Phospholipase A2, and Lipase The first stage of the process described in D above is carried out to provide a product containing phosphatidic acid, in an amount determined by reaction time and temperature and enzyme concentration.

To this product is added phospholipase A2, in an amount of 0.001 to 0.2%, based on 60% AI. If necessary, the pH is adjusted to a level favorable to the enzyme by adding Tris HCl, and $CaCl_2$ is added. Reaction is carried out at about 40–60° C. for 4 to 24 hours. Drying provides a lecithin product containing lysophospholipid, lysophosphatidic acid, and, optionally, phosphatidic acid, in amounts determined by reaction time and temperature and enzyme concentration.

To this product is added a lipase, in an amount of 0.001 to 0.2%, preferably 0.1 to 0.2%, based on 60% AI. If necessary, the pH is adjusted to a level favorable to the enzyme by adding Tris HCl, and $CaCl_2$ is added. Reaction is carried out at about 40–60° C. for 4 to 24 hours. Drying provides a lecithin product containing lysophospholipid, lysophosphatidic acid, and, optionally, phosphatidic acid, and also containing mono/diglycerides, in amounts determined by reaction time and temperature and enzyme concentration.

Preferably, the lipase concentration and other parameters are effective to produce a hydrolyzed lecithin product containing at least 15%, and more preferably at least 30%, mono/diglycerides.

In a variation of reactions employing phospholipase D, an alcohol selected from ethanolamine, L-serine, inositol, and a choline salt is included in the reaction mixture with phospholipase D, to vary the distribution of phospholipids (i.e. the PE/PS/PI/PC ratio) in the final product.

F. Hydrolysis in Organic Solvent; Single Enzyme

A fluid lecithin obtained as the retentate from a membrane degumming process, as described, for example, in U.S. Pat. No. 6,207,209, having an acetone insoluble (AI) level of 55%–80%, is combined with a triglyceride selective lipase, which may be immobilized, in an amount of about 0.1 to 0.2% based on 60% AI. If necessary, the pH is adjusted to a level favorable to the enzyme by adding Tris HCl, and $CaCl_2$ is added. Excess $CaCl_2$ may be used to efficiently sequester released fatty acids. Reaction is carried out at about 20–60° C. for 1 to 24 hours. In a preferred embodiment, the reaction is carried out in the presence of a membrane having a composition and pore size effective to selectively remove fatty acids from the reaction mixture.

Immobilized enzyme is recovered, and drying provides a lecithin product containing mono/diglycerides, in an amount determined by reaction time and temperature and respective enzyme concentration. Preferably, the lipase concentration and other parameters are effective to produce a hydrolyzed lecithin product containing at least 15%, and more preferably at least 30%, mono/diglycerides.

What is claimed as new and desired to be protected by Letters Patent of the United States is:

1. A method of producing a hydrolyzed lecithin product, comprising hydrolyzed phospholipids, monoglycerides, and diglycerides, the method comprising
   (a) contacting a lecithin material, comprising phospholipids and triglycerides, in an aqueous medium, containing water and at most 5% of another water-miscible solvent, or an organic solvent medium comprising an aprotic organic solvent and sufficient water to promote hydrolysis, with a first enzyme to create a reaction mixture, said enzyme being a phospholipase or lipase which hydrolyzes said phospholipids;
   (b) subsequently contacting the product of step (a), in an aqueous medium or an organic solvent medium containing sufficient water to promote hydrolysis, with a second enzyme, different from said first enzyme, said second enzyme being a lipase which hydrolyzes said triglycerides; and
   (c) obtaining the hydrolyzed lecithin product from the reaction mixture.

2. The method of claim 1, wherein said phospholipids make up at least 50% of said lecithin material.

3. The method of claim 2, wherein said phospholipids make up at least 60% of said lecithin material.

4. The method of claim 1, wherein said first enzyme is phospholipase A1 and/or A2.

5. The method of claim 4, wherein said phospholipase is phospholipase A2.

6. The method of claim 1, wherein said second enzyme is effective to selectively hydrolyze said triglycerides.

7. The method of claim 1, wherein said solvent medium is an aqueous medium and does not contain another water-miscible solvent.

8. The method of claim 1, wherein said solvent medium comprises an organic solvent.

9. The method of claim 8, wherein said organic solvent is a hydrocarbon solvent.

10. The method of claim 9, wherein said solvent is hexane.

11. The method of claim 1, wherein said lecithin material is a retentate from a vegetable oil membrane degumming process.

12. The method of claim 1, wherein steps (a) and (b) are carried out in the presence of a membrane effective to separate said hydrolyzed phospholipids, monoglycerides, and diglycerides from released fatty acids.

13. The method of claim 8, wherein steps (a) and (b) are carried out in the presence of a membrane effective to separate said hydrolyzed phospholipids, monoglycerides, and diglycerides from released fatty acids.

14. The method of claim 1, wherein said first enzyme is phospholipase D.

15. The method of claim 14, further comprising, prior to said contacting step (b), reacting the product of step (a) with phospholipase A1 and/or A2.

16. The method of claim 1, wherein said hydrolyzed lecithin product comprises at least 56% acetone insoluble materials and has an acid value of less than 45 mg KOH/gram.

17. The method of claim 16, wherein said hydrolyzed lecithin product comprises at least 60% acetone insoluble materials.

18. A method of producing a hydrolyzed lecithin product, comprising hydrolyzed phospholipids, monoglycerides, and diglycerides, the method comprising
   contacting a lecithin material, comprising phospholipids and triglycerides, in an aprotic organic solvent containing sufficient water to promote hydrolysis, with first and second enzymes to create a reaction mixture, wherein said first enzyme is a phospholipase or lipase which hydrolyzes said phospholipids, and said second enzyme, different from said first enzyme, is a lipase which hydrolyzes said triglycerides; and obtaining the hydrolyzed lecithin product from the reaction mixture.

19. The method of claim 18, wherein said lecithin material is contacted with said first and second enzymes simultaneously.

20. The method of claim 18, wherein said phospholipids make up at least 50% of said lecithin material.

21. The method of claim 20, wherein said phospholipids make up at least 60% of said lecithin material.

22. The method of claim 18, wherein said first enzyme is phospholipase A1 and/or A2.

23. The method of claim 22, wherein said phospholipase is phospholipase A2.

24. The method of claim 18, wherein said second enzyme selectively hydrolyzes said triglycerides.

25. The method of claim 18, wherein said lecithin material is a retentate from a vegetable oil membrane degumming process.

26. The method of claim 18, wherein said contacting is carried out in the presence of a membrane effective to separate said hydrolyzed phospholipids, monoglycerides, and diglycerides from released fatty acids.

27. The method of claim 18, wherein said product comprises at least 56% acetone insoluble materials and has an acid value of less than 45 mg KOH/gram.

28. The method of claim 18, wherein said product comprises at least 60% acetone insoluble materials.

29. A method of producing a product comprising phospholipids, monoglycerides, and diglycerides by enzymatic hydrolysis, the method comprising:
   contacting a lecithin material, comprising phospholipids and triglycerides, in an aqueous medium or an organic solvent medium comprising an aprotic organic solvent and sufficient water to promote hydrolysis, and in the absence of a phospholipase, with a lipase to create a reaction mixture which selectively hydrolyzes said triglycerides; and obtaining the hydrolyzed lecithin product from the reaction mixture, wherein said lecithin material is a retentate from a vegetable oil membrane degumming process.

30. The method of claim 29, wherein said solvent medium is an organic solvent medium.

31. The method of claim 29, wherein said phospholipids make up at least 50% of said lecithin material.

32. The method of claim 29, wherein said phospholipids make up at least 60% of said lecithin material.

33. The method of claim 29, wherein said hydrolyzed lecithin product comprises at least 56% acetone insoluble materials and has an acid value of less than 45 mg KOH/gram.

34. The method of claim 33, wherein said hydrolyzed lecithin product comprises at least 60% acetone insoluble materials.

35. A method of producing a product comprising phospholipids, monoglycerides, and diglycerides by enzymatic hydrolysis, the method comprising:

contacting a lecithin material, comprising phospholipids and triglycerides, in an aqueous medium or an organic solvent medium comprising an aprotic organic solvent and sufficient water to promote hydrolysis. and in the absence of a phospholipase, with a lipase to create a reaction mixture which selectively hydrolyzes said triglycerides; and obtainina the hydrolyzed lecithin product from the reaction mixture, wherein said contacting is carried out in the presence of a membrane effective to separate said phospholipids, monoglycerides, and diglycerides from released fatty acids.

36. The method of claim 35, wherein said solvent medium is an organic solvent medium.

37. The method of claim 35, wherein said lecithin material is a retentate from a vegetable oil membrane degumming process.

38. The method of claim 35, wherein said phospholipids make up at least 50% of said lecithin material.

39. The method of claim 35, wherein said phospholipids make up at least 60% of said lecithin material.

40. The method of claim 35, wherein said hydrolyzed lecithin product comprises at least 56% acetone insoluble materials and has an acid value of less than 45 mg KOH/gram.

41. The method of claim 40, wherein said hydrolyzed lecithin product comprises at least 60% acetone insoluble materials.

\* \* \* \* \*